United States Patent [19]
Knapp et al.

[11] Patent Number: 5,395,614
[45] Date of Patent: Mar. 7, 1995

[54] **PROTECTIVE *PLASMODIUM FALCIPARUM* HYBRID PROTEINS WHICH CONTAIN PART-SEQUENCES OF THE MALARIA ANTIGENS HRPII AND SERP, THE PREPARATION AND USE THEREOF**

[75] Inventors: Bernhard Knapp; Erika Hundt; Burkhard Enders; Hans Küpper, all of Marburg, Germany

[73] Assignee: Behringwerke Aktiengesellschaft, Marburg, Germany

[21] Appl. No.: 152,922

[22] Filed: Nov. 16, 1993

Related U.S. Application Data

[63] Continuation of Ser. No. 17,446, Feb. 12, 1993, abandoned, which is a continuation of Ser. No. 806,471, Dec. 13, 1991, abandoned.

[30] Foreign Application Priority Data

Dec. 24, 1990 [DE] Germany ............... 40 41 836.7

[51] Int. Cl.⁶ ............... A61K 39/015; C07K 15/08
[52] U.S. Cl. ............... 424/272.1; 424/191.1; 424/192.1; 424/269.1; 435/69.3; 435/69.7; 530/402; 530/403; 530/806
[58] Field of Search ............... 424/88, 191.1, 192.1, 424/269.1, 272.1; 514/2; 435/69.3, 69.7; 530/350, 395, 403, 806, 820

[56] References Cited

U.S. PATENT DOCUMENTS

| | | | |
|---|---|---|---|
| 4,859,465 | 8/1989 | Rutter | 424/89 |
| 4,957,738 | 9/1990 | Patarroyo | 424/88 |
| 5,130,416 | 7/1992 | Wellems | 530/350 |

FOREIGN PATENT DOCUMENTS

| | | | |
|---|---|---|---|
| 0254862 | 3/1988 | European Pat. Off. | A61K 39/015 |
| 0275196 | 7/1988 | European Pat. Off. | |
| 0283882 | 9/1988 | European Pat. Off. | |
| 0315085 | 5/1989 | European Pat. Off. | |
| 0322712 | 7/1989 | European Pat. Off. | |
| WO88/02757 | 4/1988 | WIPO | |
| 8802757 | 4/1988 | WIPO | C07K 15/12 |
| 9001549 | 2/1990 | WIPO | C12N 15/30 |

OTHER PUBLICATIONS

Cox, F. E. G., TIBTECH 9:389–394 (Nov., 1991), "Malaria vaccines—progress and problems".

Crisanti, A., et al., Science 240:1324–1326 (3 Jun. 1988), "Epitopes recognized by ells map within the conserved part of the GP190 of *P. falciparum*".

Groux, H., et al., Eur. J. Immunol. 20:2317–2323 (1990), "Functional characterization of the antibody–mediated protection against blood stages of *Plasmodium falciparum* in the monkey *Saimiri sciureus*".

(List continued on next page.)

*Primary Examiner*—Christine M. Nucker
*Assistant Examiner*—Thomas Cunningham
*Attorney, Agent, or Firm*—Finnegan, Henderson, Farabow, Garrett & Dunner

[57] ABSTRACT

Protective *Plasmodium falciparum* hybrid proteins which contain part-sequences of the malaria antigens HRPII and SERP, the preparation and use thereof.

The invention relates to hybrid proteins composed of part-sequences of the malaria antigens HRPII and SERP. The HRPII sequence has already proven protective in the monkey model (EP-A2-0 315 085), where a C-terminal region of 189 amino acids has been used in the present invention in the same way as in the preceding protection experiment. SERP was identified with the aid of an antiserum against a protective protein band (EP-A1-0 283 882); the part-sequence used (amino acids (AA) 631–892 or 630–764) contains at least two T-cell epitopes (Roussilhon et al. (1990), Immunol. Letters 25, 149–154). In preferred embodiments, further T-cell epitope-containing regions of other *P. falciparum* proteins such as merozoite surface antigen I (MSA I or else "195 kd antigen"), amino acids from 100 to 300, are incorporated (Crisanti et al. (1988), Science 240, 324–326). The property common to all the hybrid components is that they represent highly conserved peptide sequences. Protection against a malaria infection is generated by immunization with abovementioned hybrid proteins.

12 Claims, 5 Drawing Sheets

OTHER PUBLICATIONS

Herrera, S., et al., P.N.A.S. (USA) 87:4017–4021 (May, 1990), "Immunization of Aotus monkeys with *Plasmodium falciparum* blood-stage recombinant proteins".

Knapp, B., et al., Mol. Biochem. Parasitol. 32:73–84 (1989), "Molecular cloning, genomic structure and localization in a blood stage antigen of *Plasmodium falciparum* characterized by a serine stretch".

Knapp, B., et al., Behring Inst. Mitt. 88:147–156 (Feb., 1991), "A recombinant hybrid protein as antigen for an anti-blood stage malaria vaccine".

Mitchell, G. H., Parasitol. 98:S29–S47 (1989), "An update on candidate malaria vaccines".

Odink, K. G., et al., FEBS Lett. 173(1):108–112 (1984), "Expression of cloned cDNA for a major surface antigen of *Plasmodium falciparum* merozoites".

Wellems, T. E., et al., P.N.A.S. (USA) 83:6065–6069 (Aug., 1986), "Homologous genes encode two distinct histidine-rich proteins in a cloned isolate of *Plasmodium falciparum*".

Knapp, B. et al., "A Recombinant Hybrid Proteins as Antigen Foran Anti-Blood Stage Malaria Vaccine", 4th Intl. Erlangen Workshop on Molecular Aspects of Immunological Host-Parasite Interactions, Erlangen, Germany, Sep. 27–29, 1990.

Cox, F. E. G., (1991), Trends in Biotech., 9:389–394.

Knapp, B. et al., (1989), Med. Biochem. Parasitol. 32:73–84.

Herrera, S. et al., (1990), Proc. Natl. Acad. Sci. USA 87:4017–4021.

Remaut, E. et al., (1981), Gene 15:81–93.

Holder, A. M. et al., (1988), Parasitology 97:373–382.

B. Knapp et al., Behring Inst. Mitt. 88:147–156 (1991).

C. Roussilhon et al., Immunology Letters, 25:149–154 (1990).

A. Crissanti et al., Science 240:1324–1326 (1988).

T. Wellems et al., PNAS USA 83:6065–6069 (Aug. 1986).

Responses Of T Cells From Sensitized Donors To Recombonant And Synthetic Peptides Corresponding To Sequences Of The *Plasmodium falciparum* SERP Antigen, Rousilnon et al., Imunol. Letters 25, 149–154 (1990).

Epitopes Recognized By Human T Cells Map Within The Conserved Part Of The GP190 Of *P. falciparum*, Crisanti et al., Science 240, 324–326 (1988).

Characterization Of Foot-And-Mouth Diseases Virus Gene Products With Antisera Against Bacterially Synthesized Fusion Proteins, Strebel et al., J. Virol. 57, 893–991 (1986).

Tightly Regulated Tac Promoter Vectors Useful For The Expression Of Unfused Proteins In *Escherichia coli*, Aman et al., Gene 69, 301–315 (1988).

A Histidine Alanine Rich Recombinant Antigen Protects Aotus Monkeys From *P. falciparum* Infection, Knapp et al., Behring Inst. Mtt. 82, 349–359 (1988).

Molecular Cloning: A Laboratory Manual, 2nd. Edn., Sambrook et al., Cold Spring Harbor Laboratory Press, (1989).

Malarial Proteinase?, Higgins et al., Nature 340, 604 (1989).

Engineering Hybrid Genes Without The Use Of Restriction Enzymes: Gene Splicing By Overlap Extension, Horton et al., Gene 77, 61–68 (1989).

PROTECTIVE *PLASMODIUM FALCIPARUM* HYBRID PROTEINS WHICH CONTAIN PART-SEQUENCES OF THE MALARIA ANTIGENS HRPII AND SERP, THE PREPARATION AND USE THEREOF

This application is a continuation of application Ser. No. 08/017,446, filed Feb. 12, 1993, now abandoned, which is a continuation of application Ser. No. 07/806,471, filed Dec. 13, 1991, abandoned.

The invention relates to hybrid proteins composed of part-sequences of the malaria antigens HRPII and SERP. The HRPII sequence has already proven protective in the monkey model (EP-A2-0 315 085), where a C-terminal region of 189 amino acids has been used in the present invention in the same way as in the preceding protection experiment. SERP was identified with the aid of an antiserum against a protective protein band (EP-A1-0 283 882); the part-sequence used (amino acids (AA) 631–892 or 630–764) contains at least two T-cell epitopes (Roussilhon et al. (1990), Immunol. Letters 25, 149–154). In preferred embodiments, further T-cell epitope-containing regions of other *P. falciparum* proteins such as merozoite surface antigen I (MSA I or else "195 kd antigen"), amino acids from 100 to 300, are incorporated (Crisanti et al. (1988), Science 240, 324–326). The property common to all the hybrid components is that they represent highly conserved peptide sequences. Protection against a malaria infection is generated by immunization with abovementioned hybrid proteins.

In view of the importance of malaria as one of the most widespread tropical diseases, the provision of an effective vaccine is of very great importance. Vaccines can be directed against sporozoites, merozoites or gametocytes of Plasmodia (P.), and in this case antigens of the asexual stage in blood (merozoites) of *P. falciparum* have been chosen.

The nucleotide and protein sequence of SERP is described in European Patent Application EP-A1-0 283 882 as that for the "140 kd protein". For example, the amino acid sequence 630 to 892 of SERP of *P. falciparum* strain FCBR is:

MetGluPheLeuGlnIleIleGluAspTyrGlyPheLeu-ProAlaGluSerAsnTyrPro TyrAsnTyrValLysValGly-GluGlnCysProLysValGluAspHisTrpMetAsnLeu TrpAspAsnGlyLysIleLeuHisAsnLysAsnGluProAsn-SerLeuAspGlyLysGly TyrThrAlaTyrGluSerGluArg-PheHisAspAsnMetAspalaPheValLysIleIle LysThr-GluValMetAsnLysGlySerValIleAlaTyrIleLysAla-GluAsnValMet GlyTyrGluPheSerGlyLysLysValGl-nAsnLeuCysGlyAspAspThrAlaAspHis AlaValAs-nIleValGlyTyrGlyAsnTyrValAsnSerGluGlyGluLys-LysSerTyr TrpIleValArgAsnSerTrpGlyProTyrTrp-GlyAspGluGlyTyrPheLysValAsp MetTyrGlyProTh-rHisCysHisPheAsnPheIleHisSerValValIlePheAsnVal AspLeuProMetAsnAsnLysThrThrLysLysGluSer-LysIleTyrAspTyrTyrLeu LysAlaSerProGluPheTyr-HisAsnLeuTyrPheLysAsnPheAsnValGlyLysLys Asn-LeuPheSerGluLysGluAspAsnGluAsnAsnLysLysLeu-GlyAsnAsnTyrIle IlePheGlyGlnAspThrAlaGlySer-GlyGlnSerGlyLysGluSerAsnThrAlaLeu GluSerAla (SEQ ID NO:5). HRPII is described in European Patent Application EP-A2-0 315 085; the nucleic acid sequence and the protein encoded thereby are contained in Tab. 2 therein. For example, an acid sequence 364 to 552 of the HRP-II antigen is:

HisValAlaAspAlaHisHisAlaHisHisAlaAlaAs-pAlaHisHisAlaHisHisAla AlaAspAlaHisHisAlaHi-sHisAlaAlaTyrAlaHisHisAlaHisHisAlaAlaAsp AlaHi-sHisAlaHisHisAlaHisHisAlaAlaAspAlaHisHisAlaHi-sHisAlaAla AspAlaHisHisAlaHisHisAlaAlaAspAlaHi-sHisAlaHisHisAlaAlaAspAla HisHisAlaHi-sHisAlaAlaAspAlaHisHisAlaHisHisAlaSerAspAlaHi-sHis AlaAlaAspAlaHisHisAlaAlaTyrAlaHisHisAlaHi-sHisAlaHisHisAlaSer AspAlaHisHisAlaAlaAspAlaHi-sHisAlaAlaTyrAlaHisHisAlaHisHisAla AlaAspAlaHi-sHisAlaAlaAspAlaHisHisAlaHisHisAlaThrAspAlaHi-sHis AlaHisHisAlaAlaAspAlaHisHisAlaThrAs-pAlaHisHisAlaAlaAlaHisHis GluAlaAlaThrHisCys-LeuArgHis (SEQ ID NO:6). Finally, a part-sequence of MSA I is described in European Patent Application EP-A1-0 254 862 under the name antigen 31-1 or part-protein of the 195 kd antigen (see FIG. 1 ibidem). An amino acid sequence 140 to 254 of the 195 kd or MSA I antigen is:

LysGluLeuLysTyrProGlnLeuPheAspLeuThrAsn-HisMetLeuThrLeuCysAsp AsnIleHisGlyPheLysTyr-LeuIleAspGlyTyrGluGluIleAsnGluLeuLeuTyr Lys-LeuAsnPheTyrPheAspLeuLeuArgAlaLysLeuAs-nAspValCysAlaAsnAsp TyrCysGlnIleProPheAsn-LeuLysIleArgAlaAsnGluLeuAspValLeuLysLys Leu-ValPheGlyTyrArgLysProLeuAspAsnIleLysAspAsn-ValGlyLysMetGlu AspTyrIleLysLysAsnLysLys-ThrIleGluAsnIleAsnGlu (SEQ ID NO:7).

It has emerged, surprisingly, that the hybrid proteins according to the invention have a protective effect which is stronger than that of each of the single proteins (FIGS. 1–4). As examples of the hybrid proteins according to the invention, the expression products of two constructs have been employed:

1. MS2/SERP/HRPII (contains SERP AA 631–892) and
2. SERP/MSA I/HRPII (contains MSA I AA 140–254 and SERP AA 630–764), which are depicted diagrammatically in FIG. 5. The fusion proteins in this case contain at least two T-cell epitopes. The more favorable purification process for such bi-, tri- or oligopartite hybrid constructions should be viewed in addition to the synergistic protective effect on use of the hybrid proteins according to the invention, because several highly active components of a malaria vaccine can be obtained in only a single purification process. In addition, a multicomponent vaccine reduces the risk that the vaccine will become inactive due to mutation of the pathogen.

The invention is described further in the examples which follow, where the constructs MS2/SERP/HRPII and SERP/MSA I/HRPII which are presented illustrate but do not limit the invention. Finally, the invention is specified by the claims.

EXAMPLES

Example 1

Description of the starting plasmids

The following plasmids were used to construct the hybrid antigens MS2/SERP/HRPII and SERP/MSA I/HRPII:

pUC-SERP: the vector pUC 18 contains a 5.6 kb genomic XbaI fragment which harbors the complete SERP gene (EP-A1-0 283 882; B. Knapp et al. (1989) Mol. Biochem. Parasitol. 32, 73–84).

pUC-HRPII: the vector pUC 18 contains a 600 bp fragment which codes for the C.-terminal part of the HRPII protein (EP-A2-0 315 085; B. Knapp et al. (1988) Behring Inst. Mitt. 82, 349–359).

pEX-31-1lrd: the vector pEX 31b contains a 600 bp fragment which codes for the N-terminal part of the antigen MSA I with deletion of a repetitive sequence (EP-A1-0 254 862).

pEX31: expression vector which, under the control of the PL promoter of the lambda phage, expresses 99 N-terminal amino acids of the polymerase of the MS2 bacteriophage, to which a foreign protein can be fused (K. Strebel et al. (1986) J. Virol. 57, 983–991).

pTRC99: expression vector which, under the control of the tac promoter, can express a foreign protein without fusion (E. Amann et al. (1988) Gene 69, 301–315).

Example 2

Construction of the hybrid antigen MS2/SERP/HRPII

The plasmid pUC-SERP was digested with the restriction enzymes EcoRI and PstI, and it was possible to isolate a 787 bp fragment of the SERP gene by conventional methods (J. Sambrook et al. (1989) Molecular Cloning: A Laboratory Manual, 2nd edn., Cold Spring Harbor Laboratory, Cold Spring Harbor, N.Y., USA). This DNA fragment was ligated between the EcoRI and PstI restriction sites of the vector pEX31b. POP 2136 cells (supplied by Stratagene), which harbor the CI 537 gene in their chromosome, were transformed, and single colonies were tested for their expression of the parasite-specific DNA sequence as MS2-polymerase fusion protein after heat induction by methods which have been described (B. Knapp et al., 1988 supra). Single colonies which carry the DNA fragment incorporated in the pEX31b vector express a 40 kD MS2-polymerase fusion protein which contains amino acids 631–892 of the SERP antigen. This region contains two T-cell epitopes between amino-acid positions 640 and 700 (C. Roussilhon et al. (1990) supra) and a region from amino-acid position 745 to 787, which is homologous with the consensus sequence of cystein proteinases (Higgins et al. (1989), Nature 340, 604).

In a second step, the plasmid pUC-HRPII, which has a PstI site at the 5' and at the 3' end with respect to the inserted DNA, was digested with the restriction enzyme HindIII and subsequently incubated under partial digestion conditions with the enzyme PstI (0.05 unit for 10 min at 37° C.) in order to isolate a DNA fragment of 600 bp which has a PstI site at the 5' end and a HindIII site (partial digestion) or a PstI site (complete digestion) at the 3' end. This DNA fragment was ligated between the PstI and the HindIII site of the plasmid pEX31b which harbors the 787 bp SERP fragment. In this case the reading frame of the HRPII fragment which has been ligated in coincides with that of the inserted SERP fragment. After transformation of POP 2136 cells, individual clones were cultured at 28° C. in LB medium to which 100 µg/ml ampicillin had been added, and the plasmid DNA of each clone was analysed by restriction enzyme digestion by known methods (J. Sambrook et al., supra). Clones which had inserted the required DNA fragments were stimulated to expression by described methods (B. Knapp et al., 1988) and analysed by SDS polyacrylamide gel electrophoresis. In this case the proteins were either stained with Coomassie blue or transferred to nitrocellulose in order to test them with antibodies directed against recombinant part-sequences of SERP (B. Knapp et al., 1989 supra) and HRPII (B. Knapp et al., 1988 supra). In contrast to the size of 62 kD derived from the amino-acid sequence, the fusion protein has a molecular weight of 75 kD. The cause of this is the unusual migration behavior, which has already been described, of the HRPII portion (B. Knapp et al., 1988 supra). The fusion protein contains parts of three different proteins: 99 amino acids of MS2-polymerase (AA 1–99), 262 amino acids of SERP (AA 100–361) and 189 amino acids of HRPII (AA 364–552). Amino-acid positions 362 and 363 are encoded by a linker region which derives from the cloning procedure. This hybrid gene uses the TAA codon of the HRPII fragment as its natural stop codon. The protein encoded by this hybrid gene reacts in Western blot analysis with antisera which are specific for SERP and for HRPII. This confirms that the hybrid protein contains antigenic determinants of both malaria proteins.

The hybrid protein was partially purified from 5 l of induced bacterial culture by stepwise increases in the urea concentration by described methods (B. Knapp et al., 1988 supra). In this case the hybrid protein dissolved in 7 M urea and could be dialyzed against 2 M urea—the minimum urea concentration to keep the protein in solution. Rabbits were immunized with the partially purified hybrid protein. Antibodies directed against the hybrid protein react both with SERP and with HRPII to approximately equal extents, as was demonstrated by Western blot analysis with P. falciparum schizont proteins.

Example 3

Construction of the hybrid antigen SERP/MSA I/HRPII

Oligonucleotides p1 (5'-CGTCCCATGGAATTCT-TACAAATTATTGAA-GAT-3', NcoI restriction site at the 5' end, complementary to bases 2641–2667 of the SERP gene) and p2 (5'-TCCTTCGCTATT-CACATAATTACCATAACCAACAATAT-TAACTGCATG-3', complementary to bases 2993–3045 of the SERP gene), and 10 ng of the pUC-SERP plasmid DNA were employed in a polymerase chain reaction (PCR). The PCR was carried out by a standard protocol using the Gen Amp TM kit (supplied by Perkin Elmer Cetus). This resulted in an approximately 400 bp fragment which codes for 135 amino acids of the SERP antigen (AA 630 to 764)—a region which contains two T-cell epitopes of the SERP antigen (C. Roussilhon et al., 1990 supra).

10 ng of the pEX-31-1lrd plasmid DNA were amplified in combination with oligonucleotides p3 (5'-GGTAATTATGTGAAT-AGCGAAG-GAGAACTCTTTGATTTAACCAATCATATG-3'; nucleotides 1–18 are complementary to bases 3022–3045 of the SERP gene and nucleotides 19–45 are complementary to bases 226–252 of the partial sequence 31-1rd of MSA I) and p4 (5'-GGGGTCGACGGATCCG-GTACCAAGCTTACTTCCTTCAATTAATT-CATTTATATTTGC-3', complementary to bases 538–567 of the partial sequence 31-1lrd of MSA I with SalI, BamHI, KpnI and HindIII restriction sites at the 5' end) by means of PCR. The 360 bp fragment resulting from this codes for 115 amino acids of the MSA I antigen (AA 140–254). This region is highly conserved in different P. falciparum strains and carries two T-cell epitopes (Crisanti et al., 1988, supra).

In each case 150 ng of the DNA fragments from the 1st and the 2nd PCR were subjected to a third PCR in combination with oligonucleotides p1 and p4 by the method of Hortom et al. (Gene 77, 61–68, 1989). The amplified 760 bp fragment was digested with the restriction enzymes NcoI and SalI and inserted between the NcoI and SalI sites of the vector pTRC99 using standard methods (J. Sambrook et al., 1989 supra). This resulted in cloning into the pTRC vector of a hybrid gene which codes for parts of the SERP and of the MSA I antigen. In this case the start codon is part of the SERP antigen, i.e. this construct has no N-terminal fusion to a non-malaria-specific sequence. In total, the fused gene codes for at least 4 T-cell epitopes.

In order to check whether this hybrid gene actually is expressed, the constructed plasmid was transformed into competent DH5α E. coli cells and induced by isopropyl thiogalactoside (IPTG) as described by Amann et al. (1988, supra). The induced cells were harvested by centrifugation, and the protein pattern was analysed by SDS PAGE. The proteins were stained with Coomassie blue or transferred to nitrocellulose which was incubated with antibodies against SERP and against the MSA I antigen. The protein pattern shows that, after induction, a 28 kD protein is expressed in high yield. This protein is a hybrid protein composed of 135 amino acids of SERP and 115 amino acids of the MSA I antigen. It has a positive reaction in Western blots with antisera against SERP and against the MSA I antigen. The plasmid construct which is composed of the pTRC vector and the hybrid gene was called plasmid pTC.

In order to be able to clone in restriction fragments of other P. falciparum antigens, irrespective of their reading frame, the polylinker of the pTC vector was replaced by the polylinker of the vectors pTRC99A, B and C (Amann et al., 1988, supra). For this, the vector pTC was digested with HindIII and subsequently the HindIII restriction site was filled in at the 3' end with nucleotides using T4 DNA polymerase by known methods (J. Sambrook et al., 1989, supra). This vector was subsequently digested with ScaI, resulting in an 830 bp fragment which was separated from the vector DNA by gel electrophoresis. The vector DNA was eluted from the gel. At the same time, the vectors pTRC99A, B and C were digested with NcoI and subsequently the 5' protruding ends were filled in with T4 DNA polymerase. Restriction of the three vectors with ScaI resulted in each case in an 890 bp fragment which was separated from the vector DNA by gel electrophoresis. This 890 bp NcoI-ScaI fragment of the vectors pTRC99A, B and C was cloned into the pTC vector residue. This resulted in the plasmids pTC1, pTC2 and pTC3 which harbor the polylinker of the pTRC vector in the three different reading frames.

The pUC-HRPII plasmid DNA was digested with the restriction endonucleases BamHI and HindIII. This resulted in a DNA fragment of 610 bp which was purified by gel electrophoresis. At the same time, the vector pTC2 was treated with the same restriction enzymes and dephosphorylated. The HRPII specific DNA fragment was ligated into the pTC2 vector by described methods (J. Sambrook et al., 1989, supra). After transformation of DH5α cells, individual colonies were cultured at 37° C. on LB agar plates which contain 100 μg/ml ampicillin. Plasmid DNA from some of these colonies was isolated and examined by restriction with BamHI and HindIII for insertion of the HRPII fragment. Positive colonies were shaken at 37° C. overnight and subsequently induced with 1 mM IPTG for 2 hours. Harvesting of the bacteria suspension by centrifugation was followed by analysis of the protein pattern by SDS PAGE. In this case the proteins were either stained directly with Coomassie blue or they were transferred to nitrocellulose and tested with antibodies against SERP, against MSA I and against HRPII. The bacteria express an additional protein band of 62 kD, which reacts in Western blots with antisera against the three malaria proteins SERP, MSA I and HRPII. This hybrid antigen is tripartite and carries 135 amino acids of SERP, 115 amino acids of the MSA I antigen and 189 amino acids of the HRPII antigen. The amino acids in positions 251 to 265 are encoded by the linker region.

Example 4

Protection experiments in the aotus model a. Individual components HRPII and 31-1lrd (fragment which contains the MSA I region used) 9 aotus monkeys (bodyweight 1000–1500 g, male and female animals bred by Behringwerke AG) were randomized and divided into 3 groups each of 3 animals (group A, B, C).

All 3 animals in group A were immunized subcutaneously three times at intervals of 3 weeks with 100 μg each time of an MS2/HRPII fusion protein (dissolved in PBS). Used as adjuvant was a 10% admixture of 50% Al(OH)$_3$+45% lecithin+5% saponin with the antigen.

The 3 animals in group B were immunized with MS2 fusion protein which contains amino acids 26–66 and 106–258 of MSA I by the same schedule.

3 animals in the infection control group (group C) each received one injection of PBS+adjuvant without antigenic component, likewise in accordance with the abovementioned schedule.

b. Individual component SERP 8 aotus monkeys (bodyweight 1000–1500 g, male and female animals bred by Behringwerke AG) were randomized and divided into 2 groups each of 4 animals (group D, E ).

All 4 animals in group D were immunized subcutaneously three times at intervals of 3 weeks with a combination of SERP regions AA 68–184 and AA 631–892, both expressed as MS2 fusion proteins (100 μg per fusion protein and dose, dissolved in PBS/3M urea). Used as adjuvant was a 10% admixture of 50% Al(OH)$_3$+45% lecithin+5% saponin with the antigen.

4 animals in the infection control group (group E) each received one injection of solvent+adjuvant without antigenic component, likewise in accordance with the abovementioned schedule.

c. MS2/SERP/HRPII hybrid protein 4 aotus monkeys (bodyweight 1000–1500 g, male and female animals bred by Behringwerke AG) were randomized and divided into 2 groups each of 2 animals (group F, G).

The 2 animals in group F were immunized subcutaneously three times at intervals of 3 weeks with, on each occasion, 100 μg of the hybrid protein (dissolved in PBS/3M urea). Used as adjuvant was a 10% admixture of poly-alpha-olefin with the antigen.

2 animals in the infection control group (group G) each received one injection of PBS/3M urea+adjuvant without antigenic component, likewise in accordance with the abovementioned schedule.

d. MS2/SERP/HRPII and SERP/MSA I/HRPII hybrid proteins 9 aotus monkeys (bodyweight 1000–1500 g, male and female animals bred by Behringwerke AG) were randomized and divided into 3 groups each of 3 animals (group H, I, K).

All 3 animals in group H were immunized subcutaneously three times at intervals of 3 weeks with, on each occasion, 100 μg of the MS2/SERP/HRPII hybrid protein (dissolved in PBS/3M urea). Used as adjuvant was a 10% admixture of poly-alpha-olefin with the antigen. The 3 animals in Group I were immunized the same schedule with the SERP/MSA I/HRPII hybrid protein.

The 3 animals in the infection control group (group K) each received one injection of PBS/3M urea+adjuvant without antigenic component, likewise in accordance with the abovementioned schedule.

All the animals in groups A-K were splenectomized 1 week after the last immunization and, about 1 week later, received a loading infection of $5 \times 10^6$ (A–G) or $2 \times 10^6$ (H–K) parasitized erythrocytes ex vivo (*P. falciparum* palo alto).

BRIEF DESCRIPTION OF THE DRAWINGS

Legend

Example 4

P. %=% parasitemia
d=days after infection
Th=therapy
Ch.=challenge (infection with *P. falciparum*, stress on the immunization)

FIG. 1A shows the results of the aotus model protection experiments for monkeys immunized with HRPII.

FIG. 1B shows the results of the aotus model protection experiments for monkeys immunized with MSA I.

FIG. 1C shows the results of the aotus model protection experiments for the control monkeys immunized with PBS and adjuvant without antigenic component.

FIG. 2D shows the results of the aotus model protection experiments for monkeys immunized with SERP.

FIG. 2E shows the results of the aotus model protection experiments for the control monkeys immunized with solvent and adjuvant without antigenic component.

FIG. 3F shows the results of the aotus model protection experiments for monkeys immunized with MS2/SERP/HRPII hybrid protein.

FIG. 3G shows the results of the aotus model protection experiments for the control monkeys immunized with PBS/3M urea and adjuvant without antigenic component.

FIG. 4H shows the results of the aotus model protection experiments for monkeys immunized with MS2/SERP/HRPII hybrid protein.

FIG. 4I shows the results of the aotus model protection experiments for monkeys immunized with SERP/MSA I/HRPII hybrid protein.

FIG. 4K shows the results of the aotus model protection experiments for the control monkeys immunized with PBS/3M urea and adjuvant without antigenic component.

FIG. 5(1) describes diagrammatically the construct of MS2, SERP and HRPII (plasmid pEX SERP/HRPII), with a linker of 2 amino acids being incorporated between SERP and HRPII.

FIG. 5(2) correspondingly describes diagrammatically the plasmid pTC2 HRPII.

aa=amino acids

---

What is claimed is:

1. A hybrid protein derived from portions of the *P. falciparum* SERP and HRP-II antigen sequences consisting of the amino acid residues from about 630 to about 892 of the SERP antigen and the amino acid residues from about 364 to 552 of the HRP-II antigen.

2. A protein of claim 1 further comprising additional non-*P. falciparum*-derived amino acid sequences.

Figure 1:
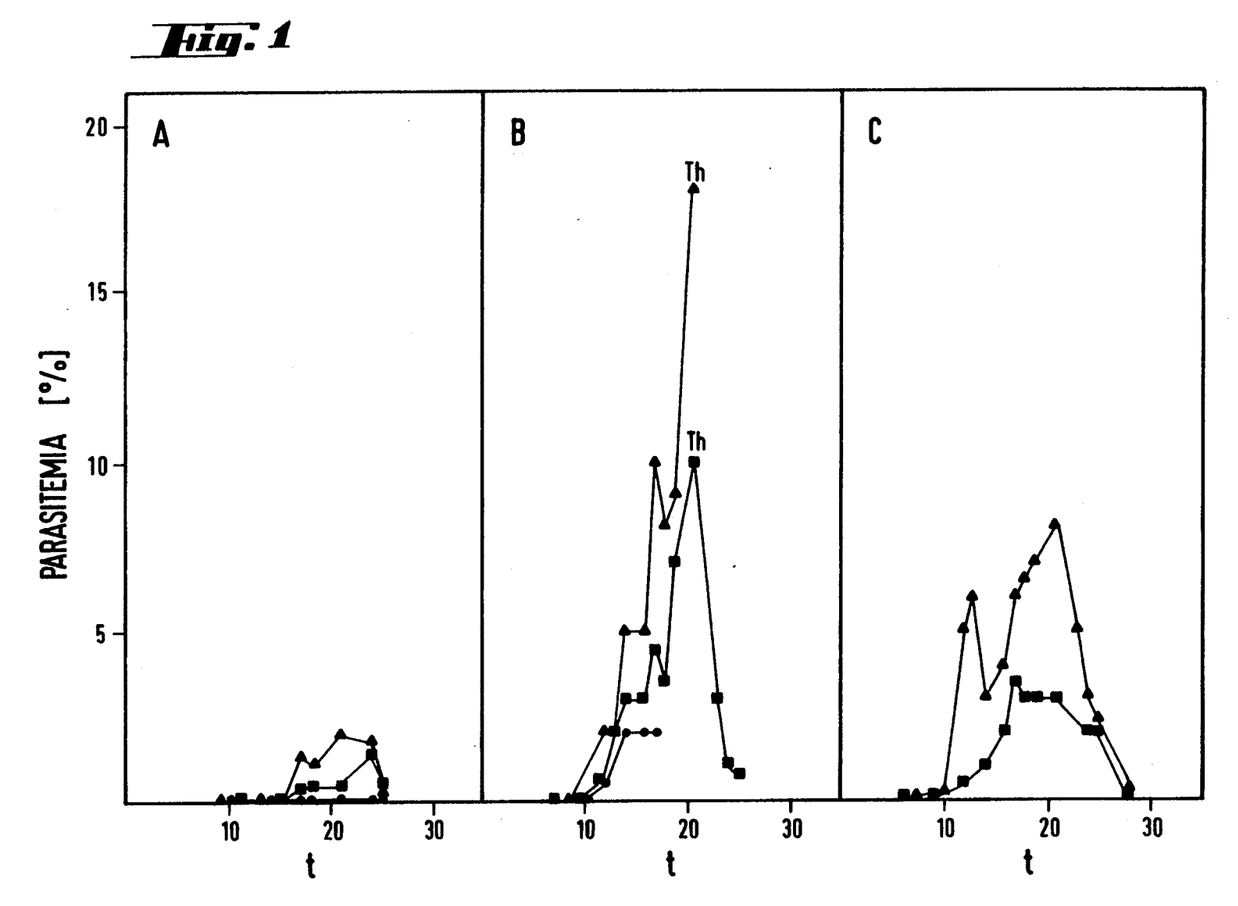
FIGS. 1–4: protection experiments in the aotus model
Figure 2A:
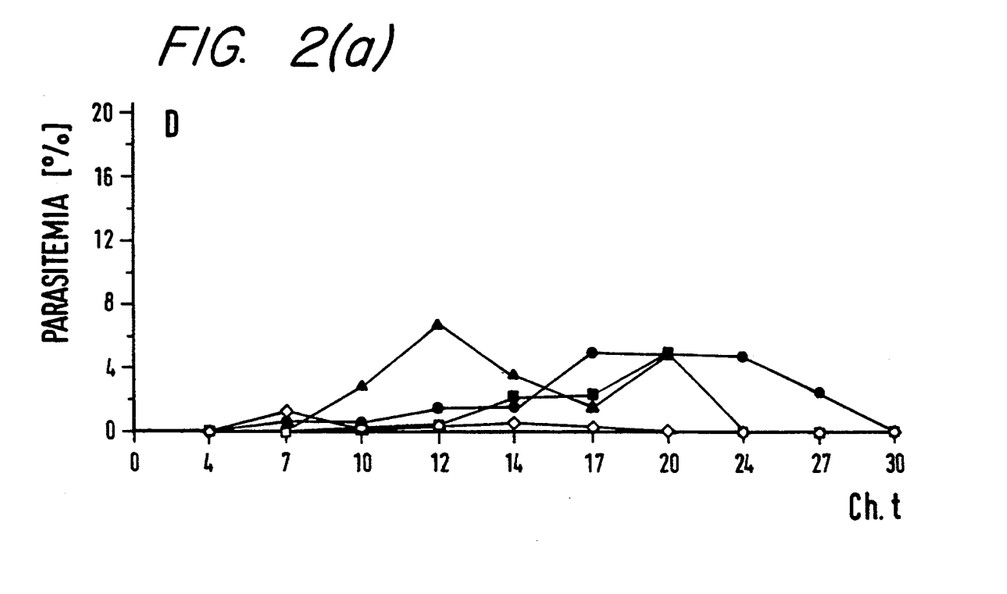
Figure 2B:
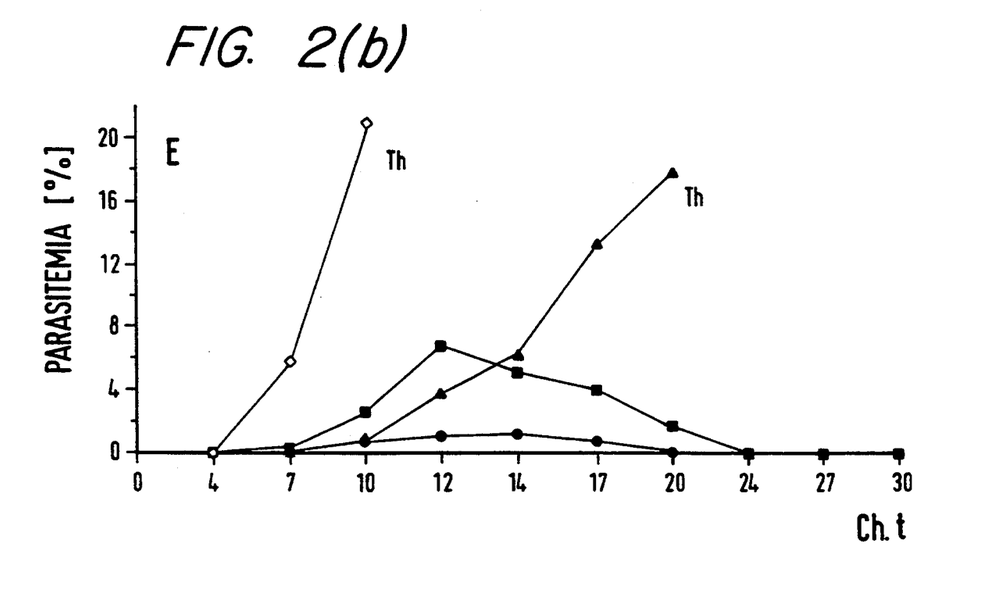
Figure 3:
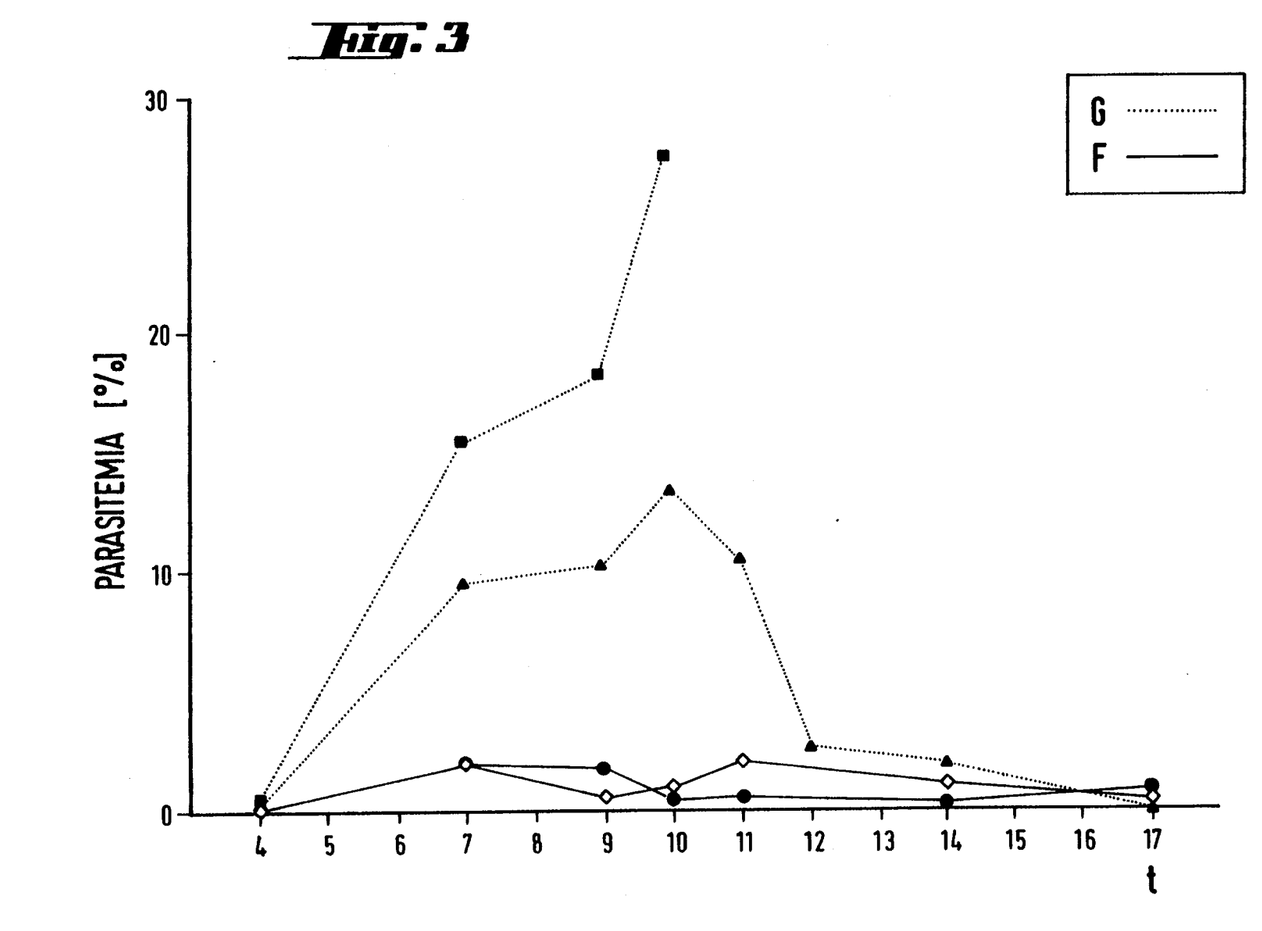
Figure 4:
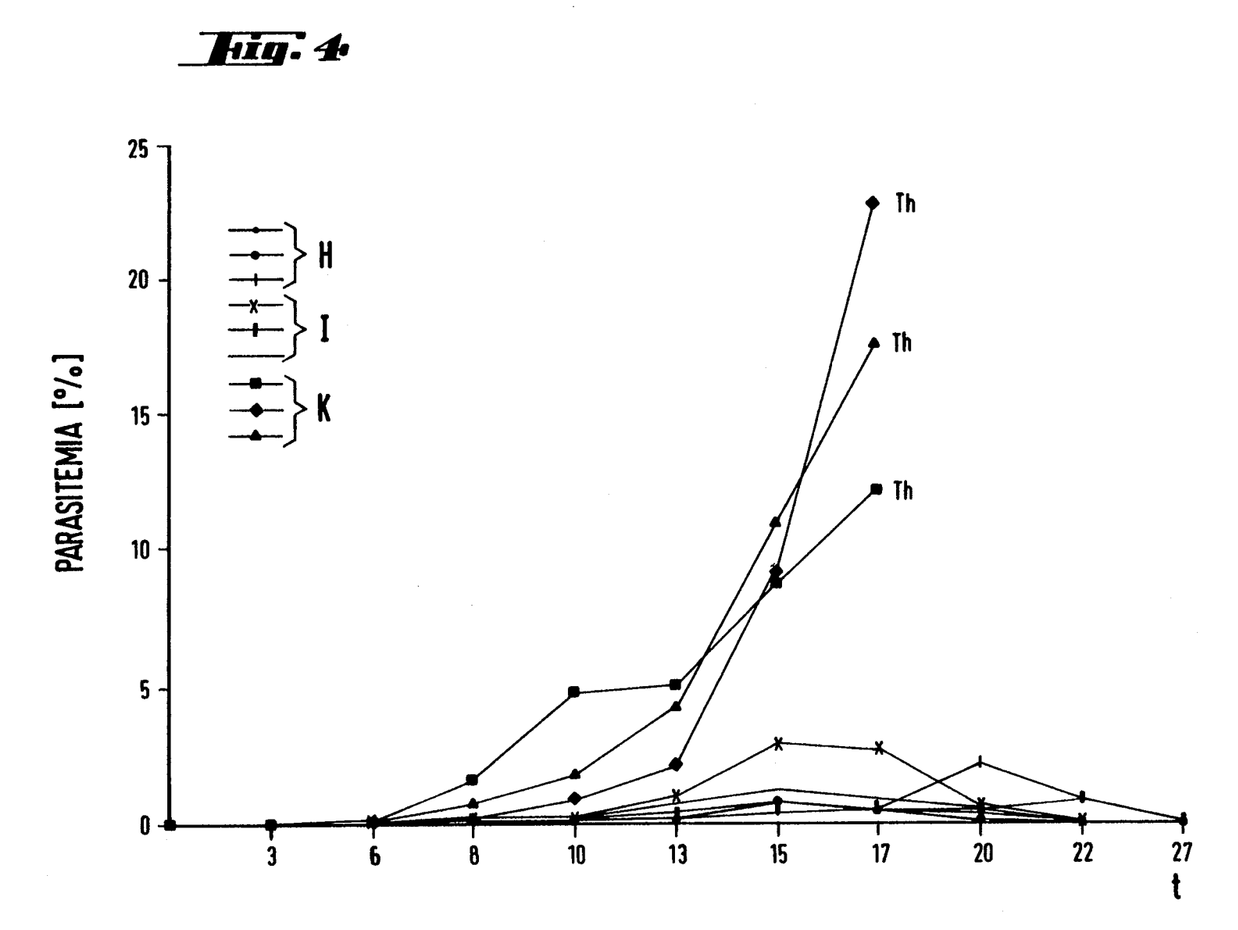
Figure 5:
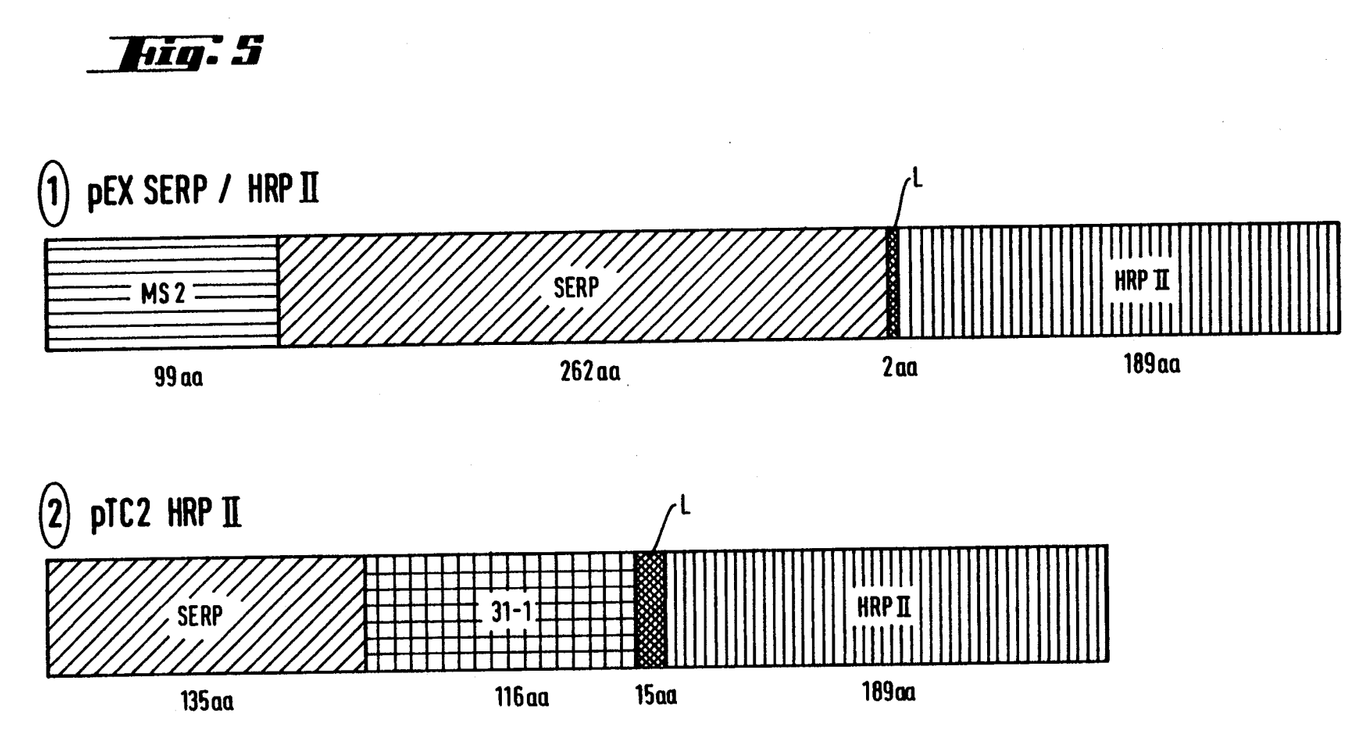

3. The MS2/SERP/HRPII fusion protein encoded by pEX SERP/HRPII as shown in FIG. 5.

4. A vaccine composition useful for reducing the severity of blood-stage malaria caused by *P. falciparum* comprising any one of the hybrid proteins of claims 1, 2, or 3, and a pharmaceutically acceptable excipient, carrier, or adjuvant.

5. A method of reducing the severity of blood-stage malaria caused by *P. falciparum* comprising administration of a vaccine composition of claim 4 to a subject.

6. A process of preparing a hybrid protein of any one of claims 1, 2, or 3 comprising (i) constructing a hybrid nucleic acid sequence which encodes a protein of any one of claims 1, 2 or 3, (ii) ligating said nucleic acid sequence into a suitable expression vector, (iii) transforming a suitable host cell with said expression vector under conditions suitable for expression of the hybrid nucleic acid sequence, and (iv) isolating a hybrid protein according to any one of claims 1, 2, or 3.

7. A hybrid protein derived from portions of the *P. falciparum* SERP, MSA I, and HRP-II antigen amino acid sequences consisting of the amino acid residues from about 630 to about 764 of the SERP antigen, the amino acid residues from about 140 to about 254 of the MSA I antigen, and the amino acid residues from about 364 to 552 of the HRP-II antigen.

8. A hybrid protein of claim 7 further comprising additional non-*P. falciparum*-derived amino acid sequences.

9. The SERP/MSA I/HRPII hybrid protein encoded by pTC2 HRPII as shown in FIG. 5.

10. A vaccine composition useful for reducing the severity of blood-stage malaria caused by *P. falciparum* comprising any one of the hybrid proteins of claims 7, 8 or 9, and a pharmaceutically acceptable excipient, carrier, or adjuvant.

11. A method of reducing the severity of blood-stage malaria caused by *P. falciparum* comprising administration of a vaccine composition of claim 10 to a subject.

12. A process of preparing a hybrid protein of any one of claims 7, 8 or 9 comprising (i) constructing a hybrid nucleic acid sequence which encodes a protein of any one of claims 7, 8 or 9, (ii) ligating said nucleic acid sequence into a suitable expression vector, (iii) transforming a suitable host cell with said expression vector under conditions suitable for expression of the hybrid nucleic acid sequence, and (iv) isolating a hybrid protein according to any one of claims 8, 9 or 10.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear     ( i i ) MOLECULE TYPE: DNA synthetic     ( x i ) SEQUENCE DESCRIPTION: SEQ ID NO:1:
        CGTCCCATGG AATTCTTACA AATTATTGAA GAT    33

( 2 ) INFORMATION FOR SEQ ID NO:2:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear     ( i i ) MOLECULE TYPE: DNA synthetic     ( x i ) SEQUENCE DESCRIPTION: SEQ ID NO:2:
        TCCTTCGCTA TTCACATAAT TACCATAACC AACAATATTA ACTGCATG    48

( 2 ) INFORMATION FOR SEQ ID NO:3:

( i ) SEQUENCE CHARACTERISTICS:
 ( A ) LENGTH: 51 base pairs
 ( B ) TYPE: nucleic acid
 ( C ) STRANDEDNESS: single
 ( D ) TOPOLOGY: linear ( i i ) MOLECULE TYPE: DNA synthetic ( x i ) SEQUENCE DESCRIPTION: SEQ ID NO:3:

```
GGTAATTATG TGAATAGCGA AGGAGAACTC TTTGATTTAA CCAATCATAT G    51
```

( 2 ) INFORMATION FOR SEQ ID NO:4:

( i ) SEQUENCE CHARACTERISTICS:
  ( A ) LENGTH: 57 base pairs
  ( B ) TYPE: nucleic acid
  ( C ) STRANDEDNESS: single
  ( D ) TOPOLOGY: linear ( i i ) MOLECULE TYPE: DNA synthetic ( x i ) SEQUENCE DESCRIPTION: SEQ ID NO:4:

```
GGGGTCGACG GATCCGGTAC CAAGCTTACT TCCTTCAATT AATTCATTTA
TATTTGC                                                      57
```

( 2 ) INFORMATION FOR SEQ ID NO:5:

( i ) SEQUENCE CHARACTERISTICS:
  ( A ) LENGTH: 263 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:5:

```
Met Glu Phe Leu Gln Ile Ile Glu Asp Tyr Gly Phe Leu Pro Ala Glu
  1               5                  10                  15

Ser Asn Tyr Pro Tyr Asn Tyr Val Lys Val Gly Glu Gln Cys Pro Lys
             20                  25                  30

Val Glu Asp His Trp Met Asn Leu Trp Asp Asn Gly Lys Ile Leu His
         35                  40                  45

Asn Lys Asn Glu Pro Asn Ser Leu Asp Gly Lys Gly Tyr Thr Ala Tyr
 50                      55                  60

Glu Ser Glu Arg Phe His Asp Asn Met Asp Ala Phe Val Lys Ile Ile
 65                  70                  75                  80

Lys Thr Glu Val Met Asn Lys Gly Ser Val Ile Ala Tyr Ile Lys Ala
                 85                  90                  95

Glu Asn Val Met Gly Tyr Glu Phe Ser Gly Lys Lys Val Gln Asn Leu
                100                 105                 110

Cys Gly Asp Asp Thr Ala Asp His Ala Val Asn Ile Val Gly Tyr Gly
            115                 120                 125

Asn Tyr Val Asn Ser Glu Gly Glu Lys Lys Ser Tyr Trp Ile Val Arg
130                 135                 140

Asn Ser Trp Gly Pro Tyr Trp Gly Asp Glu Gly Tyr Phe Lys Val Asp
145                 150                 155                 160

Met Tyr Gly Pro Thr His Cys His Phe Asn Phe Ile His Ser Val Val
                165                 170                 175

Ile Phe Asn Val Asp Leu Pro Met Asn Asn Lys Thr Thr Lys Lys Glu
                180                 185                 190

Ser Lys Ile Tyr Asp Tyr Tyr Leu Lys Ala Ser Pro Glu Phe Tyr His
            195                 200                 205

Asn Leu Tyr Phe Lys Asn Phe Asn Val Gly Lys Lys Asn Leu Phe Ser
            210                 215                 220

Glu Lys Glu Asp Asn Glu Asn Asn Lys Lys Leu Gly Asn Asn Tyr Ile
225                 230                 235                 240

Ile Phe Gly Gln Asp Thr Ala Gly Ser Gly Gln Ser Gly Lys Glu Ser
                245                 250                 255
```

Asn Thr Ala Leu Glu Ser Ala
            260

(2) INFORMATION FOR SEQ ID NO:6:

(i) SEQUENCE CHARACTERISTICS:
       (A) LENGTH: 189 amino acids
       (B) TYPE: amino acid
       (D) TOPOLOGY: linear (ii) MOLECULE TYPE: peptide (xi) SEQUENCE DESCRIPTION: SEQ ID NO:6:

His Val Ala Asp Ala His His Ala His Ala Ala Asp Ala His His
1               5                   10                  15

Ala His His Ala Ala Asp Ala His His Ala His His Ala Tyr Ala
                20                  25                  30

His His Ala His His Ala Ala Asp Ala His His Ala His His Ala His
                35                  40                  45

His Ala Ala Asp Ala His His Ala His His Ala Ala Asp Ala His His
        50                  55                  60

Ala His His Ala Ala Asp Ala His His Ala His His Ala Ala Asp Ala
65                  70                  75                  80

His His Ala His His Ala Ala Asp Ala His His Ala His His Ala Ser
                85                  90                  95

Asp Ala His His Ala Ala Asp Ala His His Ala Ala Tyr Ala His His
                100                 105                 110

Ala His His Ala His His Ala Ser Asp Ala His His Ala Ala Asp Ala
        115                 120                 125

His His Ala Ala Tyr Ala His His Ala His His Ala Ala Asp Ala His
        130                 135                 140

His Ala Ala Asp Ala His His Ala His His Ala Thr Asp Ala His His
145                 150                 155                 160

Ala His His Ala Ala Asp Ala His His Ala Thr Asp Ala His His Ala
                165                 170                 175

Ala Ala His His Glu Ala Ala Thr His Cys Leu Arg His
                180                 185

(2) INFORMATION FOR SEQ ID NO:7:

(i) SEQUENCE CHARACTERISTICS:
       (A) LENGTH: 115 amino acids
       (B) TYPE: amino acid
       (D) TOPOLOGY: linear (ii) MOLECULE TYPE: peptide (xi) SEQUENCE DESCRIPTION: SEQ ID NO:7:

Lys Glu Leu Lys Tyr Pro Gln Leu Phe Asp Leu Thr Asn His Met Leu
1               5                   10                  15

Thr Leu Cys Asp Asn Ile His Gly Phe Lys Tyr Leu Ile Asp Gly Tyr
                20                  25                  30

Glu Glu Ile Asn Glu Leu Leu Tyr Lys Leu Asn Phe Tyr Phe Asp Leu
        35                  40                  45

Leu Arg Ala Lys Leu Asn Asp Val Cys Ala Asn Asp Tyr Cys Gln Ile
        50                  55                  60

Pro Phe Asn Leu Lys Ile Arg Ala Asn Glu Leu Asp Val Leu Lys Lys
65                  70                  75                  80

Leu Val Phe Gly Tyr Arg Lys Pro Leu Asp Asn Ile Lys Asp Asn Val
                85                  90                  95

```
Gly Lys Met Glu Asp Tyr Ile Lys Lys Asn Lys Lys Thr Ile Glu Asn
            100             105                 110
Ile Asn Glu
    115
```